United States Patent [19]

Carmon et al.

[11] 4,362,165
[45] Dec. 7, 1982

[54] STABLE GEL ELECTRODE

[75] Inventors: Amiram Carmon, Jerusalem, Israel; Kevin Claffey, Brooklyn, N.Y.; Daniel Lowe, Teaneck, N.J.; Lloyd Osipow, New York, N.Y.

[73] Assignee: IPCO Corporation, White Plains, N.Y.

[21] Appl. No.: 110,449

[22] Filed: Jan. 8, 1980

[51] Int. Cl.³ .............................. A61B 5/04
[52] U.S. Cl. .................... 128/640; 128/803
[58] Field of Search .............. 128/639–641, 128/644, 803

[56] References Cited

U.S. PATENT DOCUMENTS

| 2,555,037 | 5/1951 | Jensen | 128/639 |
|---|---|---|---|
| 2,886,564 | 5/1959 | Holysz | 128/803 X |
| 3,027,333 | 3/1962 | Friedman | 128/803 X |
| 3,518,984 | 7/1970 | Mason | 128/640 |
| 3,567,657 | 3/1971 | Lichtenstein | 128/803 X |
| 3,572,323 | 3/1971 | Yuan | 128/640 |
| 3,587,565 | 6/1971 | Tatoian | 128/640 |
| 3,607,788 | 9/1971 | Adolph et al. | 128/640 |
| 3,710,782 | 1/1973 | Hauser | 128/639 |
| 3,862,094 | 1/1975 | Shinohara et al. | 252/500 |
| 3,901,218 | 8/1915 | Buchalter | 128/641 |
| 3,961,623 | 6/1976 | Milani et al. | 128/803 |
| 3,989,035 | 11/1976 | Zuehlsdorff | 128/641 |
| 3,989,050 | 11/1976 | Buchalter | 128/803 |
| 3,993,049 | 11/1976 | Kater | 128/640 |
| 3,998,215 | 12/1976 | Anderson et al. | 128/641 |
| 4,016,869 | 4/1977 | Reichenberger | 128/640 |
| 4,027,664 | 6/1977 | Heavner, Jr. et al. | 128/641 |
| 4,066,078 | 1/1978 | Berg | 128/641 |
| 4,094,822 | 6/1978 | Kater | 128/640 X |
| 4,102,331 | 7/1978 | Grayzel | 128/640 |
| 4,109,648 | 8/1978 | Larke et al. | 128/639 |
| 4,125,110 | 11/1978 | Hymes | 128/641 |
| 4,257,424 | 3/1981 | Cartmell | 128/641 |

FOREIGN PATENT DOCUMENTS

| 1965195 | 12/1969 | Fed. Rep. of Germany | 128/640 |
|---|---|---|---|
| 2727396 | 12/1978 | Fed. Rep. of Germany | 128/803 |

Primary Examiner—Lee S. Cohen
Attorney, Agent, or Firm—Pennie & Edmonds

[57] ABSTRACT

A disposable electrode comprising an annulus of foam, a substantially uniform electrode gel in a central region of the annulus, a conductive layer in the electrode gel and making electrical contact with it, and a cap over the conductive layer, electrode gel and annulus of foam. The electrode is made in a plastic tray by placing said annulus in a recess in the tray, placing the conductive layer on the annulus, pouring hot electrode gel into the center region of the annulus, covering the gel with the cap and covering the tray with a sheet whcih is heat sealed to the tray with the electrode inside.

9 Claims, 4 Drawing Figures

STABLE GEL ELECTRODE

CROSS REFERENCE TO RELATED APPLICATIONS

Related applications, filed concurrently herewith, are "Disposable Electrode And Its Method of Manufacture", Ser. No. 110,446, now U.S. Pat. No 4,317,278, and "Highly Stable Gel, Its Use and Manufacture", Ser. No. 110,450, now U.S. Pat. No. 4,318,746, both of which are assigned to the assignee of the present application and are incorporated herein by reference.

BACKGROUND ART

This concerns a disposable electrode and a method for its manufacture.

Electrodes are used in numerous medical applications either for monitoring or stimulation or for both. For example, they are used to pickup bioelectric signals in electrocardiography and electroencephalography. They are used for electrical stimulation in pain control devices and in defibrillators. Whatever their application, it is necessary that the electrodes provide for good electrical contact with the patient's skin and good electrical signal transmission between the patient and electrical leads to the monitoring or from the stimulation devices.

Typically, a bioelectric electrode comprises a lead wire leading to or from an electrical apparatus and an interface medium between this lead wire and the patient's skin. The interfacing medium is the crucial element in the electrode, since it has to answer a rigid set of requirements. Such requirements are that the medium be a good conductor, be physically conforming to the skin surface, adhere strongly to skin, and retain these characteristics over a considerable period of time.

Typically, the medium used in most electrodes is a conductive semiliquid get which can be made according to large numbers of formulations, such as those set forth in U.S. Pat. No. 3,027,333 to Friedman, and in U.S. Pat. No. 3,567,657 to Lichtenstein, or other formulas available from numerous commerical sources. A semiliquid gel has several disadvantages, the most serious is that it is messy and tends to seep out from a pad in which it is impregnated (such a pad is described in U.S. Pat. No. 3,998,215 to Anderson and Gumbusky) or from the open cells of a polymeric sponge in which the gel is trapped such as described in U.S. Pat. No. 3,901,218 to Buchalter in U.S. Pat. No. 3,989,035 to Zuchisdorff and in U.S. Pat. No. 4,027,664 to Heavner et al.

The instability of the semiliquid gel led to the invention of other alternatives for an interfacing medium which could eliminate the messiness and seepage of the gel. For example, a self drying conductive collodium was proposed by Adolph in U.S. Pat. No. 3,607,788. A more solid gel, having a consistency of Mayonaise was proposed by Buchalter in U.S. Pat. No. 3,989,050.

Still other solutions involve the use of rigid conductive gels, which could be self supporting, i.e., could be used as a sheet of material placed between the conductive wire and the skin. Such material made of high consistency gel, resembling rubber pads, can conform to the skin surface, and their material does not spill or disintegrate. Moreover, some rigid gels have the additional characteristic of tackiness, i.e., they adhere well to the skin and eliminate, totally or partially, the need for adhesive elements which are used conventionally around the gel-wire combination in an attempt to provide firm contact. The need for this is apparent because in many cases the electrode has to stay for long periods on the skin (as in electrocardiographic monitoring) or stay on the skin when the patient moves vigourously (as in electrocardiographic ergometry). Tacky, rigid gels have been proposed by Berg (U.S. Pat. No. 4,066,078), who devised a gel made of carboxylic esters and sulphated cellulose esters, plasticised by glycerol. Another alternative is that proposed by Hymes (U.S. Pat. No. 4,125,110), where a combination of a naturally occuring polysaccharide, namely Karaya, and hydric alcohol were used to form a sheet of rigid gelatinous material.

The teaching of the last two patents cited are that the end result is satisfactory as long as one considers the tackiness and the conformity characteristics. However, the conductivity is not always the desirous one for electrocardiographic monitoring, as in the case of the Karaya which is referred to in the Hymes patent.

Furthermore, the preparation of electrodes made from these type of rigid gel is a relatively complex and lengthy process, when compared to the electrode preparation using liquid or semiliquid gel. In the last case, the gel is simply poured into a cavity or onto a nonwoven material used to trap the gel. In the case of the rigid sheets of gels, the gel has to be processed first into large sheets, cured and dried, and only then it is cut into smaller pieces to fit the lead wire, or lead pad. Since a very important characteristic of disposable electrodes is their low cost, improvement in the gel preparation can be a considerable advantage.

DISCLOSURE OF THE INVENTION

The present invention describes an electrode which is especially adapted for use with an interfacing material which is liquid in nonambient high temperature (e.g., 85° C.), and therefore pourable in such temperatures, but which becomes, within less than a minute, a rigid gel, when subjected to ambient temperature (less than, e.g., 60° C.). Thus, when poured from the container in which it is held in the liquid state, it can form without further treatment into a pad. This fast and simple operation has obvious advantages over a gel curing process.

Preferably the gel used is that described in the above-referenced application entitled "Highly Stable Gel, its Use and Manufacture". As described in greater detail therein, such a gel has the advantage of being a good conductor, with good conformity to skin surface and high stability with respect to both these characteristics, in addition to the ease of its manufacture. The gel has also a high degree of tackiness, which does not change significantly when the patient perspires. Furthermore, the gel is also very stable across repeated cycling in high (e.g., 80° C.) or low, freezing temperature, which makes it ideal for storage.

The present invention describes in detail the use of this type of gel in bioelectrodes, and the mode of manufacturing of such electrodes with this particular gel. As will become apparent when reading the details of the invention, the electrodes which are obtained are much simpler in nature and cheaper in production than those obtained with the use of liquid gels, and the process of their manufacture is easier than with some other rigid gels.

GENERAL PRINCIPLES OF STRUCTURE

The two main components of the preferred electrodes are (1) a firm, conductive and adhesive gel, which is the interface between the patient and (2) a thin strip of metal, or a strip of metal coated plastic sheet which is used as an electrical conduit to a recording or stimulating instrument, and which is imbedded in the gel. Two additional components can be used: to add firmer support to the electrode gel, the pad of gel may be surrounded by (3) a reinforcing frame made of soft and conforming plastic material; and to add adhesiveness to the electrode this frame of plastic material can be coated on one side with adhesive layer. A sealed plastic cap (4) can be mounted onto the other side of the frame to decrease the drying of the gel by sealing it off from the air.

DETAILS OF EACH COMPONENT

1. The Gel

Under normal temperatures, the gel has the form of a semi-rigid sheet, i.e., under normal handling it will not spread, or break into pieces. It is flexible enough to conform loosely to any body surface it adheres to and it has cohesive and adhesive properties.

When this gel is brought to nonambient high temperature its consistency is fluidic and nonadhesive; and when it is poured out from a container heated to such temperatures, in a very short time it assumes the characteristics outlined above of a semirigid, conforming and adhesive pad. This change in physical state as a function of temperature permits low cost manufacturing.

The electrode gel and its method of manufacture is the subject of the above-referenced patent application entitled: "Highly Stable Gel, its Use and Manufacture". It is composed of two polymers, one of which is hot water soluble and the other of which is not, said polymers being combined in hot water. The hot water soluble polymer is preferably kappa carrageenan; and the hot water insoluble polymer is hydroxypropylmethylcellulose (HPMC). For enhancing its electrical conductivity, as well as augmenting cross linking of the polymer, the gel may include potassium salts such as potassium chloride or potassium carbonate.

2. The Metal Conductor

The preferred conductor in biomonitoring (e.g., electrocardiographic) electrodes is composed of two layers. A layer of silver chloride is in direct contact with the gel and under it is a layer of silver. The two layers eliminate the electrode potential which has an order of magnitude high enough to interfere with very low bioelectric signals. For a stimulating electrode, the same combination of metals on any other conductive material, such as metal or carbon is conventionally used.

Preferably, the conductor is made by coating a thin plastic sheet, such as Mylar, or a metal sheet, such as brass, with the conductive metal(s). This coating can be achieved in several ways, i.e., ion-implantation, metal sputtering or by painting the plastic sheet with metal containing epoxy paint. When the sheet is coated by silver, the outer surface of the silver can be easily chloridized into silver chloride, therefore achieving the recommended silver-silver chloride combination. The precoated sheet is cut into separate conductors. The shape of the conductor is preferably that of a narrow strip, and it is mostly imbedded in the gel, leaving only a short tab projecting outside to be connected to a wire running to the recording or stimulating instrument.

3. The Plastic Reinforcing-Adhesive Frame

In order to protect the outside perimeter of the molded gel sheet from undue wear and tear, the sheet is surrounded by a reinforcing plastic frame which has soft, body conforming characteristics. Preferably, the plastic frame is made of polyvinyl closed cell foam. To augment the adhesiveness of the electrode, the frame is coated on its underside with adhesive paste. A similar coating on the top side is used to adhere the sealing cap to the same foam on the top side.

4. The Sealing Cap

Since the gel includes a high proportion of water it may dry up even in normal humidity conditions when exposed to the air. Though the rate of drying is relatively slow (30% loss of weight by water evaporation in 6 hours) it is desirable to seal the gel from the air. When the plastic frame is used, a small piece of thin plastic sheet is cut into a shape whose edges will cover the outside perimeter of the frame and is attached to the adhesive layers pasted on the frame. In a preferred embodiment, such a cap is made of a piece of thin Mylar or vinyl.

Preferably, the electrodes are formed in plastic trays. An annulus of foam is placed in each tray, a conductive layer is fitted into the center region of the annulus, hot electrode gel is poured into this center region, and a cap is placed over the foam, the gel, and the conductive layer. The tray is then sealed with a cover sheet to form an airtight package in which the electrode may be shipped and stored.

BRIEF DESCRIPTION OF THE DRAWING

These and other objects, elements and features of the invention will be more readily apparent from the following detailed description of the invention in which.

BEST MODE OF CARRYING OUT THE INVENTION

Figure 1:
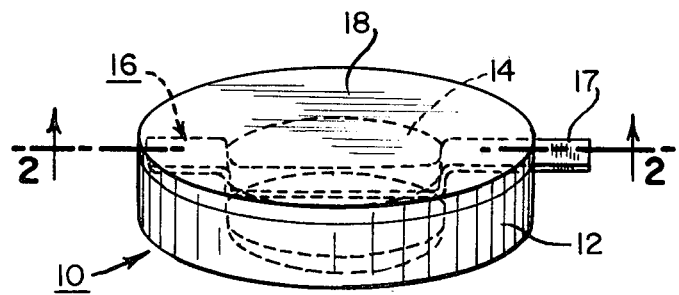
FIG. 1 depicts an illustrative embodiment of an electrode made in accordance with the invention.
Figure 2:
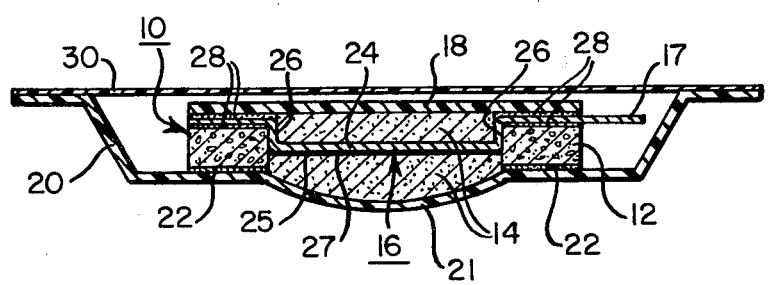
FIG. 2 is a cross-sectional view (not to scale) of the embodiment of FIG. 1 along lines 2—2.

As shown in FIGS. 1 and 2 a preferred embodiment of an electrode 10 of the present invention comprises an annulus of foam 12, an electrode gel 14 in the interior of the annulus, a conductive layer 16 in the gel, and a vinyl cap 18 covering the conductive layer, electrode gel and foam. For manufacturing and storage purposes, the electrode is mounted on a plastic tray 20 and an adhesive layer 22 secures the electrode to the tray. As shown in FIG. 2 a dimple 21 protrudes outward from the bottom of tray 20 so that the electrode gel likewise protrudes beyond the surface of foam annulus 12. For purposes of illustration, the protrusion of dimple 21 has been exaggerated in FIG. 2. In practice, it is about 1/32 inch (0.8 mm.) for an electrode that is about 1½ inch (38 mm.) wide. This construction has been found to permit better contact between the gel and the patient's skin and better adhesion of the electrode to the patient's skin. Conductive layer 16 comprises a substrate 24 that is coated on at least one side with a silver layer 25; and in the area where the silver layer makes contact with the gel the silver layer is coated with a layer of silver chloride 27. As shown, a tab 17 that is an integral part of conductive layer 16 extends out over the outer edge of foam 12. This tab provides for connection to the electrode as described below and illustratively is shaped to mate with the female half of a spade connector. As is apparent from FIG. 3, the conductive layer is an elongated strip that is generally rectangular in shape and is formed with a central depression 26 and two outer flanges that rest on opposite sides of the upper surface of the foam annulus. When the gel is poured into the center region of the annulus, the gel is warm enough that it flows over the depressed portion 26 of the conductive layer. As a result, when the gel cools, the conductive layer is securely fastened in the gel. An adhesive layer 28 on the underside of cap 18 secures the cap to foam 12 and the upper surface of conductive layer 16. For shipping and storage purposes the tray in which the electrode is mounted is covered by a plastic sheet 30 which is heat sealed to peripheral flanges of tray 20 to form an airtight enclosure.

Advantageously the foam is ⅛ inch (3 mm.) thick, 2 pounds (1 kg.) density Volara. For monitoring electrodes, the conductive layer is 20 mil (0.5 mm.) thick brass coated on both major surfaces with a 0.2 to 0.5 mil (0.005 to 0.013 mm.) thick layer of silver and a surface film of silver chloride. For electrodes which can be used during both monitoring and defilbrillation, the conductive layer preferably is 0.2 to 0.5 mil (0.005 mm. to 0.013 mm.) Mylar polyester film with a 0.5 mil (0.0125 mm.) thick layer of silver on one side and a surface film of silver chloride on the silver coat. If desired, the conductive layer may be strengthened by an additional layer of a material such as vinyl or another plastic. Illustratively, the conductive layer is about 3/16 inch (5 mm.) wide or less. Cap 18 is about 12 mils (0.3 mm.) thick. Tray 20 is 15 mil polyethylene or polypropylene and sheet 30 is a composite made of thin layers of paper, polyethylene (or polypropylene), foil and polyethylen (or polypropylene).

The exterior diameter of the foam annulus typically is about 1½ inch (38 mm.) and the width of the foam annulus is about 5/16 inch (8 mm.). In the preferred embodiment illustrated in FIG. 1, the foam annulus is substantially planar and the interior region defined by the foam annulus is a cylindrically shaped space having a height of ⅛ inch (3 mm.) and a diameter of 13/16 inch (20 mm.) in which the electrode gel is located. For a foam annulus of these dimensions, tray 20 is about 2½×2½ inches (63×63 mm.) with a 2×2 inch (51×51 mm.) recess. Dimple 21 is a depression in the recess of the tray that is about 13/16 inch across and about 1/32 inch (0.8 mm.) deep. The conductive layer is about 2 inches (51 mm.) long and is positioned so that one end of it extends well beyond the outer edge of the foam annulus. The central section of the conductive layer is depressed about 1/16 inch (1.5 mm.) to form a depression 26 that fits into the center region of the annulus. Advantageously, depression 26 is about 13/16 inch (20 mm.) long to facilitate proper positioning of the conductive layer in the annulus. As will be apparent to those skilled in the art, electrodes of all different sizes and shapes may be made in accordance with my invention simply by varying the size and shape of the peripheral foam layer that defines the region in which the electrode gel is located.

Fabrication of an electrode in this process depends on the use of an electrode gel which is relatively rigid and adhesive at ordinary temperatures but which will flow readily at elevated temperatures. To meet these requirements, the electrode gel comprises:

a first polymer that dissolves, hydrates or disperses in hot water and that forms or can be made to form a rigid gel on cooling, a hot water insoluble polymer that dissolves or hydrates on cooling and is compatible with said first polymer, and water, said polymers being combined in hot water.

Water is the major constituent of the gel and in the preferred embodiment accounts for more than 90% of the weight of the gel. Preferably the first polymer is carrageenan in weight percentage of about 0.5 to 5.0%; and the hot water insoluble polymer is a non-ionic cellulose derivative such as hydroxypropylmethylcellulose (HPMC) in weight percentage of about 2 to 20%. Preferably, the electrode gel also contains an electrolyte such as potassium chloride or potassium carbonate. Such a gel flows at elevated temperatures and is rigid at temperatures below about 60° to 65° C. Further details concerning this gel and its manufacture are set forth in the concurrently filed application incorporated herein by reference. As noted in said application, since carrageenan is conductive itself, a separate electrolyte need not be used in some applications of this disposable electrode.

Figure 3:
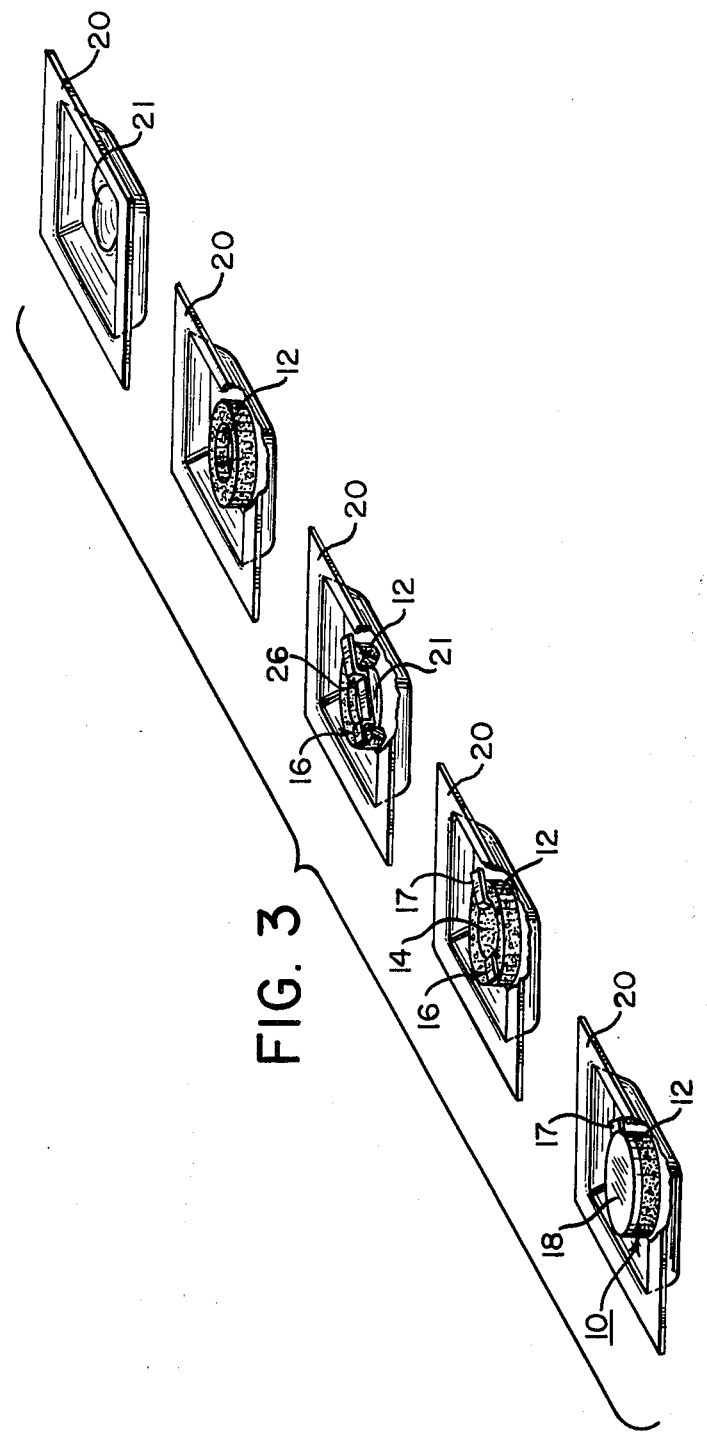
FIG. 3 is a schematic illustration of the steps involved in manufacturing the electrode of FIG. 1.

As shown in FIG. 3, in which the same numbers are used to identify the corresponding elements of FIGS. 1 and 2, electrode 10 is advantageously manufactured in plastic tray 20. First, foam annulus 12 is secured by adhesive layer 22 (FIG. 2) to the bottom of tray 20 approximately centered on dimple 21 protruding below the tray. Next, a conductive layer 16 is placed on the foam annulus. The conductive layer is long enough that it extends well beyond the outer edge of the foam annulus and depression 26 is sized so that it fits snuggly into the center region of the annulus. The electrode gel at a temperature of about 85 degrees C. is then poured into the center region of the foam annulus. Since the electrode gel is liquid at this temperature, the gel flows over the conductive layer and surrounds it. When the gel cools and becomes rigid, this produces a strong physical bond and a good electrical connection between the conductive layer and the gel 14. A vinyl cap 18 is then placed on top of the gel to keep it from drying out. Advantageously, the cap may also cover the upper surface of the foam and the flanges of the conductive layer resting on the foam and the cap may be secured to the foam by an adhesive layer 28 (FIG. 2). Finally, tray 20 is covered by a plastic sheet and the sheet is heat sealed to the peripheral flanges of tray 20.

Advantageously, for machine assembly of these electrodes, the trays can be formed in a continuous strip of plastic; the operations of inserting the foam into the tray, placing the conductive layer on the foam, pouring the gel, applying the cap, and sealing on cover sheet 30 can be performed automatically; and the individual trays can then be separated one from the other.

To use, one simply peels cover 30 from tray 20 and removes electrode 10 from the tray by grasping the edge of the foam annulus and pulling. A mating swivel connector or a spade connector may then be slipped onto tab 17 and electrode 10 may be secured to the patient's skin. Since the gel protrudes beyond the surface of the foam, the electrode provides better contact and adhesion to the patient's skin.

Figure 4:
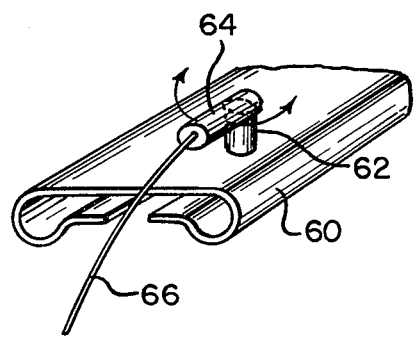
FIG. 4 is a schematic illustration of a connector advantageously used with the electrode of FIGS. 1 and 2.

An illustrative example of a swivel electrode suitable for use with electrode 10 is set forth in FIG. 4. As shown therein, the connector comprises a conventional spring clip 60, a post 62 and a receptacle 64 suitable for receiving an electrical lead 66. The mounting of receptacle 64 and post 62 is such that receptacle 64 can swivel with respect to clip 60. The provision of such swivel action in the connector reduces the chance that movement of the patient will tear the electrode from his skin; and by putting the swivel in the connector rather than the electrode, the cost of the electrode is significantly decreased.

As will be apparent to those skilled in the art, numerous modifications may be made within the spirit and scope of the invention described herein. Different conductive layers may be used depending on the application to which the electrode is put and the shape of the conductive layers may also be varied as the occasion demands. Likewise electrodes of all sizes and shapes may readily be used in the practice of the invention; and the invention is by no means limited to the specific examples described herein.

What is claimed is:

1. A disposable electrode comprising:
   a plastic member with an aperture in a central region thereof,
   a firm, substantially uniform electrode gel in said aperture, said gel having cohesive and adhesive properties and comprising:
   water,
   a first polymer in weight percentage of at least 0.5 percent that has been dissolved, dispersed or hydrated in said water when said water is at an elevated temperature and that forms or can be made to form a rigid gel upon cooling,
   a second polymer in weight percentage of at least 2.0 percent that is insoluble in hot water, that dissolves or hydrates on cooling, that is compatible with said first polymer and that has been combined with said first polymer and water when said first polymer is dissolved, dispersed or hydrated in said water,
   a conductive layer, one portion of which is in the electrode gel making electrical contact with it and a second portion of which extends out of said gel, and
   a cap covering said aperture on one side of said plastic member.

2. A disposable electrode comprising:
   a plastic member with an aperture in a central region thereof,
   a substantially uniform electrode gel in said aperture, said gel comprising water in weight percentage of at least 50%, carrageenan in weight percentage of about 0.5 to 5.0% and a non-ionic cellulose derivative compatible with carrageenan in weight percentage of about 2% to 20%, said cellulose derivative having been combined with said carrageenan while said carrageenan is dissolved in said water,
   a conductive layer, one portion of which is in the electrode gel making electrical contact with it and a second portion of which extends out of said gel, and
   a cap covering said aperture on one side of said plastic member.

3. A disposable electrode comprising:
   a plastic frame with an aperture in a central region thereof, said frame serving as a reinforcing frame to support an electrode gel;
   a firm, substantially uniform electrode gel in said aperture surrounded by said frame, said electrode gel having cohesive and adhesive properties and comprising:
   a hot water soluble polymer in weight percentage of at least 0.5 percent that forms or can be made to form a rigid gel on cooling,
   a hot water insoluble polymer in weight percentage of at least 2.0 percent that hydrates on cooling and is compatible with said hot water soluble polymer, and
   water, said polymers having been combined in hot water;
   an electrical conductor, one portion of which is imbedded in the electrode gel and makes electrical contact with it and a second portion of which extends out of said gel, and
   a cap covering said electrode gel.

4. The electrode of any one of claims 1 through 3 wherein said gel further comprises an electrolyte.

5. The electrode of claims 1 or 2 wherein said plastic member is made of foam.

6. The electrode of claims 1 or 2 wherein said conductive layer is a metal coated strip of plastic or another metal.

7. The electrode of any one of claims 1 through 3 wherein said cap is a plastic sheet.

8. The electrode of claim 3 wherein said electrical conductor is a metal coated strip of plastic or another metal.

9. The electrode of claim 3 wherein said plastic frame is made of foam.

* * * * *